United States Patent [19]

Kiedik et al.

[11] Patent Number: 5,198,591
[45] Date of Patent: Mar. 30, 1993

[54] METHOD TO MANUFACTURE BISPHENOL A

[75] Inventors: Maciej Kiedik, Kedzierzyn-Kozle; Jozef Kolt, Zabrze; Jerzy Marszycki, Kedzierzyn-Kozle; Eugeniusz Zajac, Kedzierzyn-Kozle; Teodor Bek, Kedzierzyn-Kozle; Zbigniew Swiderski, Kedzierzyn-Kozle; Anna Rzodeczko, Kedzierzyn-Kozle; Jerzy Mroz, Kedzierzyn-Kozle; Janina Olkowska, Kedzierzyn-Kozle, all of Poland

[73] Assignees: Instytut Ciezkiej Syntezy Organicznej "Blachownia"; Zaklady Chemiczne "Blachownia", both of Kedzierzyn-Kozle, Poland; ABB Lummus Crest Inc., Bloomfield, N.J.

[21] Appl. No.: 797,428

[22] Filed: Nov. 22, 1991

[30] Foreign Application Priority Data

Nov. 24, 1990 [PL] Poland .................................. 287944

[51] Int. Cl.⁵ ........................ C07C 37/20; C07C 37/70
[52] U.S. Cl. .................................... 568/727; 568/722; 568/724; 568/728; 568/749; 568/753; 568/781; 568/782; 568/806
[58] Field of Search .............. 568/722, 727, 728, 749, 568/753, 781, 782, 806, 724; 23/295 R

[56] References Cited

U.S. PATENT DOCUMENTS

| 2,623,908 | 12/1952 | Stoesser | 568/727 |
| 3,290,390 | 12/1966 | Prahl et al. | 568/724 |
| 4,131,749 | 12/1978 | Kiekik et al. | 568/781 |
| 4,188,496 | 2/1980 | Jaquiss et al. | 568/724 |
| 4,301,305 | 11/1981 | Kiedik et al. | 568/727 |
| 4,375,567 | 5/1983 | Faler | 568/727 |
| 4,847,433 | 7/1989 | Kissinger | 568/727 |
| 4,906,789 | 3/1990 | Grzywa et al. | 568/727 |
| 4,954,661 | 9/1990 | Iimuro | 568/727 |
| 5,087,767 | 2/1992 | Okamoto et al. | |

FOREIGN PATENT DOCUMENTS

| 0210366 | 2/1987 | European Pat. Off. | |
| 0319326 | 6/1989 | European Pat. Off. | 568/724 |
| 332203 | 9/1989 | European Pat. Off. | 568/724 |
| 3833900 | 4/1989 | Fed. Rep. of Germany. | |
| 113641 | 6/1982 | Poland | 568/727 X |
| 123971 | 1/1985 | Poland | 568/727 |

OTHER PUBLICATIONS

International Search Report for PCT/PL91/00014.

Primary Examiner—Werren B. Lone
Attorney, Agent, or Firm—Chilton, Alix & Van Kirk

[57] ABSTRACT

The invention relates to a process for obtaining a high purity bisphenol from a post-reaction mixture resulting from the step of synthesis of phenol and acetone in the presence of a strong acid cation exhanger catalyst, by the way of crystallation and separation by distillation followed by recovery of bisphenol-A from the step of thermal catalytic decomposition of by product of the principal process technology in a multistage process.

20 Claims, 1 Drawing Sheet

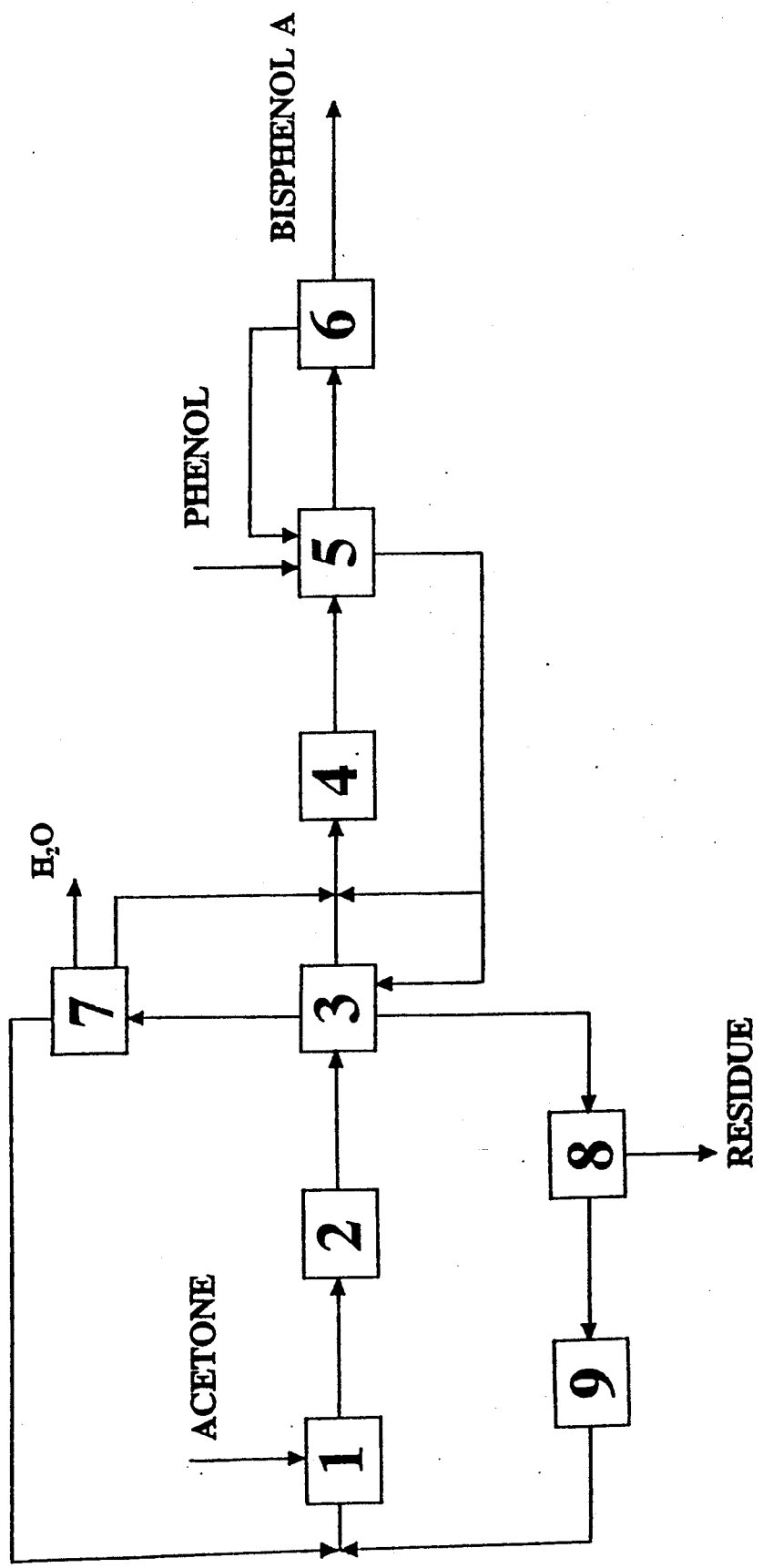

METHOD TO MANUFACTURE BISPHENOL A

BACKGROUND OF THE INVENTION

The present invention relates to a method for manufacturing high-purity 2,2'-di(4-hydroxyphenyl)-propane, also called bisphenol A. The bisphenol A is used as a feedstock for producing resins, principally epoxy and polycarbonate resins, including the optical polycarbonate grade where especially high purity and good colouration are required.

Bisphenol A is obtained from a reaction of phenol and acetone in the presence of a strong-acid cation exchanger as catalyst. The post-reaction mixture contains, besides the bisphenol A, unreacted phenol, acetone and water, or catalyst and water, and by-products, mainly 2-(4-hydroxy phenol)-2'-(2-hydroxyphenyl)-propane, i.e., ortho-para isomer of bisphenol A, the so-called o,p-isomer, 2-2-4-trimethyl-4-(4-hydroxyphenyl)-chromane, i.e. the so-called Dianin compound, trisphenols, polyphenols and coloured compounds. Depending on the methods selected for further processing the post-reaction mixture, recovery and purification of bisphenol A, the final product may contain some amount of by-products which deteriorate its purity and colouration and unfavourably affect further processing.

A number of methods for removing the impurities are known in the art. The most commonly used method is to remove acetone and water, or catalyst, acetone, water and part of phenol from the post-reaction mixture followed by recovery, by crystallization, of bisphenol-A/phenol adduct which is then separated by distillation into raw bisphenol A and phenol. The mother liquor remaining after adduct recovery, which contains primarily phenol and some by-products and dissolved bisphenol A, can be recycled to the reaction system. In a multistage process, the bisphenol A is recovered by thermal catalytic decomposition of the by-products of the principal process technology.

The Polish Patent No. P-268 149 describes a process to manufacture bisphenol A where the feed is obtained by mixing the recycled phenolic liquor with part of the post-reaction mixture collected in the reaction system. The initial concentration of bisphenol A in this feed is 12-20% wt of bisphenol A, the content of bisphenol A isomers in the total amount of by-products is less than 25% of the by-products and the phenol-to-acetone mole ratio is (5-30):1. The reaction is conducted at 60°-95° C. in the presence of a catalyst such as a mixture of macro- and microporous cation exchanger resin in the weight ratio of (0.05-0.5):1, respectively. This reaction results in a mixture containing bisphenol A at a high concentration, i.e. 21-35% wt, and 12-24% wt of by-products. Owing to the phenol liquor being recycled to the reaction system, the quantity of the impurities is increased. In order to prevent cumulation of undesirable substances in the process, the impurities are removed by withdrawal of part of the liquor stream from the reaction system and processing it as required, to recover a suitable amount of bisphenol A.

The European Patent No 3328870 describes a method to remove impurities from bisphenol A consisting of the addition of water to the post-reaction mixture following removal of the catalyst therefrom, and vacuum evaporation of the water and part of the phenol from the mixture, resulting in bisphenol-A/phenol adduct crystallization. The separated water is then contacted, as a mixture with phenol and the impurities, with a weak-basic ion-exchange resin prior to being recycled to the crystallized adduct and then on with the crystallized adduct, for further treatment. The substantial disadvantage of the method is that only a small percentage of the impurities are removed from the post-reaction mixture.

The UK Patent No 1565667 describes a method to recover bisphenol A and remove coloured impurities from all or part of the recycled mother liquor stream by contacting it with an adsorber bed in the form of a cation-exchange resin. This permits some impurities present in the mother liquor to be removed before it is recycled to the reaction system. Obviously, the volume of mother liquor which can be purified using this method is limited; furthermore, the adsorber does not adsorb all the impurities to be removed and additional regeneration is required, i.e. washing, drying and removal of impurities from the washing liquid. Thus, part of the impurities are transferred to the reaction system with the liquor being recycled, the result of which is recycled bisphenol A lower in quality than that produced in the reaction of phenol with acetone.

Some other methods for removing impurities and recovering bisphenol A from all or part of the post-crystallization liquor arising from the step of bisphenol-A/phenol adduct separation or from process by-products produced in the process for obtaining bisphenol A from their catalytic decomposition while distilling off the product being formed and recycling the waste products to the reaction are also known to those skilled in the art.

According to Polish Patents No 113641 and 103054, impurities are removed and bisphenol A is obtained with high efficiency by a method where phenol, in the presence of cation-exchanger resin catalyst, is reacted with intermediates, such as p-isopropenylphenol, o-isopropenylphenol and their dimers, obtained by thermal catalytic decomposition of bisphenol A process by-products and introduced to the reaction in phenolic solution, the said phenolic solution of synthesis by-products being dewatered post-crystallization liquor or fractions formed during distillation of the dewatered post-crystallization liquor. The reaction of phenol with the products of thermal catalytic decomposition of the bisphenol A process by-products is, according to the cited Patents, conducted in a separate reactor, under different conditions than those accompanying the phenol-acetone reaction, preferably in the presence of 5-20% by weight of water.

The methods, as described above, do not show good efficiency; part of the undesirable impurities are transferred, with the adduct, into subsequent steps of bisphenol A process.

The European Patent No 0332203 describes a method to obtain high-purity bisphenol A, comprising a principal process and a so-called sub-process. In the principal process, phenol is made to react with acetone and the post-reaction mixture is treated to obtain a solution with a desirable concentration of bisphenol A: this is the so-called step I of concentration control and is followed by step I of bisphenol A/phenol adduct crystallization, step I of adduct separation from the mother liquor and step I of phenol removal from the adduct to obtain a high-purity bisphenol A. The sub-process consists of the following: step II of phenol reaction with p-isopropenylphenol, step II of bisphenol A concentration control, step II of bisphenol-A/phenol adduct crystallization, step II of adduct crystalline fraction II separation from mother liquor II, and step II of mother liquor II processing to obtain p-isopropenylphenol and phenol, the mother liquor I from the principal process being fed to the sub-process. The adduct crystalline fraction from the sub-process is fed to the principal process.

The European Patent No EP 0332203 also claims another variant of the process to obtain a high-purity bisphenol A. The principal process comprises the following: step I of reaction where phenol is made to react with acetone and catalyst is removed, step of crystallization where bisphenol-A/phenol adduct is recovered, step of crystalline adduct separation from mother liquor, and step of phenol removal from crystalline adduct.

The sub-process consists of the following: phenol reaction with p-isopropenylphenol in the presence of an acid catalyst and catalyst removal to obtain phenolic solution II, removal of phenol from phenolic solution II to obtain crude bisphenol A, separation of low- and high-boiling substances from raw bisphenol A by distillation to obtain distilled bisphenol A, and processing of the separated low- and high-boiling substances to obtain p-isopropenylphenol and phenol. The mother liquor from the principal process is fed to the sub-process and the distilled bisphenol A from the sub-process is fed to the principal process.

The resulting bisphenol A shows high purity due to "dilution" of impurities by introduction of adduct or bisphenol A, recovered in the sub-process, to the principal process as a starting material. The main disadvantage of the process to obtain high-purity bisphenol A according to Patent No 0332203 is the complexity created by the introduction of the sub-process comprising a number of steps of a complexity comparable to that of the principal process. This results in a considerable increase in the investment and operating costs of the bisphenol A plant where the process is used.

SUMMARY OF THE INVENTION

The present invention is aimed at elaborating a process to obtain high-purity bisphenol A from post-reaction mixtures containing high concentrations of by-products, wherein the faults and disadvantages present in the known processes are not encountered.

According to the present invention the following reactions are conducted simultaneously in a reaction system comprising step I of the process: reaction of phenol with acetone, reaction of phenol with p-isopropenylphenol resulting from thermal decomposition of process by-products and recycled to the reaction system, and isomerizational rearrangement of process by-products to obtain bisphenol A in the presence of a micro- and macroporous cation-exchange resin catalyst mixture. Step II of the process comprises cooling the post-reaction mixture together with water and acetone to obtain a precipitate of bisphenol-A/phenol in phenolic solution. Step III of the process comprises separation of the precipitate into crystalline bisphenol-A/phenol adduct and phenolic mother liquor I. The crystalline adduct is washed with the phenolic liquor and step IV follows, wherein the bisphenolA/phenol adduct obtained in step III is dissolved in the phenolic solution and the resulting mixture is cooled to obtain a bisphenol-A/phenol precipitate in phenolic solution. Step V comprises separation of the precipitate obtained in step IV into the crystalline bisphenol-A/phenol adduct and mother liquor II to be turned back to step III of the process. The bisphenol-A/phenol crystalline adduct is then washed with phenolic solution and step VI follows, wherein a high-purity bisphenol A is recovered by removal of phenol from the bisphenol-A/phenol adduct obtained in step V. Step VII of the process consists in distillation of the phenolic mother liquor I obtained in step III, and removal of acetone, water and part of phenol therefrom. Dewatered phenol liquor is turned back to step I of the process to the reaction zone and step VIII follows, consisting of thermal catalytic decomposition of part of the mother liquor I obtained in step(s) III and/or VII, resulting in a distillate comprising phenol, isopropenylphenol and process by-products. Step IX consists of catalytic rearrangement of the reactive components of the distillate obtained in step VIII, while leaving the p-isopropenylphenol contained therein substantially intact and the rearranged distillate is recycled to step I of the process.

In step I, the by-products are present in the reaction system in an amount of 10–30% by weight. The content of acetone and water in the post-reaction mixture while cooling it in step II is 2–6% by weight of acetone and 1–4% by weight of water, respectively. The crystalline bisphenol-A/phenol adduct is washed in step III with mother liquor II, obtained in step V, in an amount of 0.2–2.0 parts by weight of the liquor per 1 part by weight of the crystalline adduct. The bisphenol-A/phenol adduct is dissolved in step IV using the mother liquor II obtained in step V and/or phenolic solution obtained in step VII. The crystalline bisphenol-A/phenol adduct is washed in step V with fresh and regenerated phenol obtained in step VI and used in a ratio of 1–3 parts by weight of fresh phenol per 1 part by weight of regenerated phenol. Bisphenol A is separated from the bisphenol-A/phenol adduct by vacuum distillation of a substantial volume of phenol and removal of phenolic residue from bisphenol A by steam stripping. The volume of phenol distilled off the mother liquor I in step VII is 0.1–0.3 parts by weight per 1 part by weight of mother liquor I. Mother liquor I obtained in step III of the process is sent to thermal catalytic decomposition in step VIII in an amount of 0.05–0.2 parts by weight. The catalytic decomposition is conducted in the range of temperature 200°–300° C. and in the range of absolute pressure of 1–50 mm Hg in the presence of catalysts selected from the group comprising: $Na_2HPO_2$, $NaHCO_3$, $NaOH$. The rearrangement of some of the components of the distillate from step VIII toward bisphenol A in step IX as a result of thermal catalytic decomposition of part of mother liquor I is conducted in the presence of oxalic acid used in an amount of 0.05–0.5% by weight.

BRIEF DESCRIPTION OF THE DRAWING

The FIGURE is a process flow diagram showing a preferred method to manufacture bisphenol A according to the invention.

DETAILED DESCRIPTION OF THE INVENTION

Substantially, the method of the present invention is advantageous in that the mother liquor I from step I of crystallization is sent to those steps of the process which are not directly connected with any further steps of bisphenol-A/phenol treatment and bisphenol A recovery, thus making their efficiency highly favourable. A majority of the impurities present in the process are removed with the stream of washing liquors and solutions I. This results in high purity and a high percentage of the large-grain size fraction in the bisphenol-A/phenol adduct recovered, with good efficiency, in recrystallization step which proceeds in a solution substantially free of impurities.

As is generally known, crystallization of a crystalline fraction from solutions containing more impurities results in the formation of finer grains, characterized by larger surface which is responsible for transferring the impurities. Thus, as a result of an increase in the amount of fine-grain crystals, the colouration and the content of impurities are observed to grow.

Quite unexpectedly, crystallization of the bisphenol-A/phenol adduct from phenolic solutions containing water and acetone was found to improve the purity and size of the crystals. It was also observed that recrystallization of the bisphenol-A/phenol adduct has a substantial effect on the results of its purification and that, even when washing the bisphenol-A/phenol adduct crystals repeatedly, the same result is not attained. Nevertheless, it is still purposeful to wash also the bisphenol-A/phenol adduct recovered in recrystallization step. The adduct is then rewashed, preferably using the phenol recovered in the subsequent step of phenol removal from the adduct. The phenol is comparable to commercial product, as far as its purity is concerned. The result of rewashing can be made more satisfactory if the volume of the phenol used for washing is increased, by addition of fresh phenol which is thereby introduced to the process as a starting material. Introduction of the fresh phenol, as starting material, in this stage of the process and its utilization, as described above, prior to sending it to step I of the synthesis reaction through appropriate circulating systems for post-crystallization streams and washing liquids has, additionally, a favourable effect on the efficiency of the step of bisphenol-A/phenol adduct purification. The bisphenol-A product obtained according to the present invention is characterized by higher purity than those obtained according to the conventional, industrially used methods.

EXAMPLE 1

A vertical drum reactor (D=2400 mm, H=10 m) was filled with a mixture composed of 70% microporous Wofatit-KPS cation exchanger and 30% macroporous Wofatit-PK-110 cation exchanger up to 7 m. The reaction mixture obtained by mixing the stream of dewatered post-crystallization liquor containing 8% by weight of bisphenol A and 15.5% by weight of process by-products with the reaction mixture collected from the bottom of the reactor was made to flow through the catalyst bed at 3400 kg/hr. The temperature of the mixture at the inlet to the reactor was 85° C. and its composition was as follows: bisphenol A—642.6 kg/hr, by-products—622.2 kg/hr including o,p-isomers—149.6 kg/hr, phenol—1883.6 kg/hr, acetone—231.2 kg/hr, water—20.4 kg/hr. The composition of the product obtained was the following: bisphenol A—816 kg/hr, by-products—550.8 kg/hr including o,p-isomers—163.2 kg/hr, acetone—192.2 kg/hr, water—40.8 kg/hr, phenol—1800.2 kg/hr. The resulting solution at 85° C. was cooled down to 40° C. to obtain the crystalline bisphenol-A/phenol adduct. The crystals at 1720 kg/hr were subjected to centrifugation to separate them from the mother liquor I and washed with mother liquor II at 344 kg/hr. The colouration of the 50% crystalline adduct solution was 70 APHA. The washed adduct was solved in the phenolic solution obtained as a result of distillation of the phenolic mother liquor I. The resultant solution was recooled to 39° C. to precipitate the bisphenol-A/phenol adduct crystals, the adduct was centrifuged and the mixture was rewashed using a mixture composed of 2000 kg fresh phenol and 1000 kg of regenerated phenol which produced 1376 kg/hr of bisphenol-A/phenol adduct. The colouration of the 50% crystalline adduct solution in ethanol was 5 APHA. The crystals were melted and sent to distillation column to distill a major part of phenol at 160° C. and 10 mm Hg. The remaining phenol was removed by steam distillation to obtain 940 kg of bisphenol A. The bisphenol A product shows the following properties: crystallization point: 156.8° C., colouration of 50% solution 4 APHA, o,p-isomer: trace amounts, codimer: trace amounts, trisphenol: 15 ppm, principal product: 99.96% by weight.

EXAMPLE 2

100 kg of the mother liquor I obtained according to Example 1 and remaining after crystallization and withdrawal of the crystalline adduct in step III of the process was subjected to distillation to remove acetone, water and part of phenol which were found in the following percentages by weight: acetone—0.86, water—0.26, phenol—75.68, bisphenol A—8, by-products—15.2. The stream was sent to the reaction unit described in Example 1 and mixed with part of the stream of the reaction mixture collected in the bottom of the reactor. The temperature at the inlet to the reactor was 85° C. and the composition of the feed as expressed in weight percentage was as follows: bisphenol A—20; by-products—15.2, including o,p-isomers—3.5; acetone—5.8; phenol—58.18, water—0.82. The composition of the post-reaction mixture as expressed in weight percentage in an amount of 3000 kg, was as follows: bisphenol A—35; acetone—3.8; by-products—15.8, including o,p-isomers—3.7; water—1.9; phenol—43.5.

The resulting solution was cooled to 40° C. to crystallize the bisphenol-A/phenol adduct. 778.38 kg of the crystalline adduct was centrifuged to separate it from the mother liquor I and washed with 1556.79 kg of the mother liquor II. The bisphenol-A/phenol adduct, in an amount of 778.38 kg, was then dissolved by heating it in 1082.43 kg of the mother liquor II from Example 1. The resulting solution was recooled to 39° C. to precipitate the crystalline bisphenol-A/phenol adduct which was then recentrifuged and washed with 720 kg of a mixture composed of fresh phenol and phenol recovered from the bisphenol-A/phenol adduct by distillation; the phenols had been mixed in a ratio of 1.5:1. The product obtained was 522 kg bisphenol-A/phenol adduct. The phenol was removed from the adduct as described in Example 1 as a result of which 336 kg of bisphenol A with the following parameters was obtained: crystallization point: 156.7° C., colouration of 50% solution in ethanol: 20 APHA; o,p-isomer: trace amounts; codimer: trace amounts; trisphenol: 52 ppm; principal component: 99.92% by weight.

EXAMPLE 3

Acetone, water and part of the phenol were removed from 500 g of the mother liquor I obtained in Example 1 as a result of which their percentages by weight were as follows: acetone—0.91, water—0.30, phenol—73.67, bisphenol A—9.92, by-products—15.2. The resulting dewatered liquor was subjected to thermal catalytic decomposition with simultaneous collection of the distillate, in the presence of 0.79 g of sodium hypophosphite as catalyst at 280° C. and at pressure lowered to 5 mm Hg. The resulting 395 g of distillate was then subjected to catalytic rearrangement with simultaneous redistillation in the presence of 1.185 g of oxalic acid as catalyst as 220° C. and at pressure lowered to 10 mm Hg. 315 g of redistillate was obtained where the components were present in the following percentages by weight: phenol—55.72, bisphenol A—3.24, p-isopropenylphenol—27.98; by—products—13.06.

EXAMPLE 4

650 g of dewatered phenol liquor obtained according to Example 2 was mixed with 100 g of the distillate resulting from the catalytic decomposition and rearrangement of dewatered phenolic liquor obtained according to Example 3 and, after supplementing the mixture with acetone to obtain 6.3% by weight of its total content in the mixture, the reaction was conducted in the presence of 100 g of Amberlyst-15 ion-exchange resin for 5 hrs at 75° C. with intense stirring to provide contact of the entire ion-exchange resin with the reaction solution. The post-reaction mixture obtained was found to contain 34.3% by weight of bisphenol A and 17-97% by weight of by-products including 3.96% by weight of o,p-isomer and 4.11% by weight of codimer. The resulting solution was cooled to 40° C. to crystallize the bisphenol-A/phenol adduct which was separated from the mother liquor by filtration in a centrifuge and washed with an equivalent amount of post-crystallization liquor II obtained according to Example II. The product, i.e. 260 g of crystalline bisphenol-A/phenol adduct, was dissolved by heating in 360 g of phenolic solution obtained as described in Example 2 and remaining after washing the crystalline adduct obtained in crystalization step II. The resulting solution was re-cooled to 39° C. to obtain crystalline bisphenol-A/phenol adduct which was then washed with an equivalent amount of fresh phenol and phenol removed by distillation from the adduct obtained in Example II, mixed in the weight ratio of 1.5:1. As a result, 235 g of bisphenol-A/phenol adduct was obtained and the phenol was removed from the adduct by the method of Example 1 which resulted in 152.3 g of bisphenol A with the following quality: crystallization point: 156.8° C., colouration of 50% solution in ethanol: 10 APHA, o,p-isomer: trace amounts, codimer: trace amounts, trisphenol: 35 ppm, principal component: 99.94% by weight.

The method of the present invention is illustrated in FIG. 1 showing the process block diagram.

The method of the present invention consists in conducting, simultaneously, reactions of phenol with acetone and with p-isopropenylphenol resulting from thermal catalytic decomposition of process by-products and recycled to the reaction system, and reactions of isomerizational rearrangement of process by-products to obtain bisphenol A in the presence of a micro- and macroporous catalyst mixture in reaction system 1. The post-reaction mixture is cooled to obtain a bisphenol-A/phenol slurry adduct in a phenolic solution in unit 2. The slurry is separated in unit 3 to obtain crystalline bisphenol-A/phenol adduct and phenolic mother liquor I. The crystalline adduct is washed in unit 3 using a phenolic solution, i.e. mother liquor II obtained in unit 5. The bisphenol-A/phenol adduct obtained in unit 3 is dissolved, in unit 4, in a phenolic solution, i.e. in mother liquor II obtained in unit 5 and/or phenolic solution, obtained in unit 7, which is a distillate of the mother liquor I formed in unit 3. Upon cooling the mixture to obtain crystalline bisphenol-A/phenol adduct in unit 5 the slurry is separated into crystalline bisphenol-A/phenol adduct and mother liquor II to be turned back to unit 3. The crystalline adduct is washed with the phenolic solution obtained by mixing fresh phenol with the regenerated phenol obtained in unit 6 in the ratio of 1 part by weight of the regenerated phenol per 1-3 parts by weight of the fresh phenol. The purified, molten bisphenol-A/phenol adduct is vacuum-distilled in unit 6 to obtain high-purity bisphenol A and recover a substantial part of phenol. The remaining phenol is recovered by steam stripping. The regenerated phenol is mixed with fresh phenol and used, in unit 5, to wash the bisphenol-A/phenol adduct resulting from recrystallization (unit 5). The mother liquor I obtained in crystallization (unit 3) is distilled in unit 7 to remove acetone, water and part of phenol, whereas dewatered mother liquor I is sent to synthesis unit 1. Part of mother liquor I obtained in unit(s) 3 and/or 7 is sent to unit 8 where it is subjected to thermal catalytic decomposition in the temperature range 200°-300° C. and in the pressure range 1-50 mm Hg in the presence of catalysts such as $Na_2HPO_2$, $NaHCO_3$, $Na_2CO_3$, NaOH. A distillate containing phenol, p-isopropenylphenol and process by-products is obtained. The reactive components of the distillate are subjected, in the presence of 0.05-0.5% by weight of oxalic acid, to catalytic rearrangement toward bisphenol A leaving the p-isopropenylphenol contained therein substantially intact, in unit 9. The distillate, rearranged in unit 9, is turned back to reaction unit 1.

We claim:

1. A process to obtain high-purity bisphenol A from a post-reaction mixture resulting from the step of synthesis from phenol and acetone, in the presence of a strong acid cation-exchanger catalyst, by way of crystallization and separation by distillation followed by recovery of bisphenol A from the step of thermal catalytic decomposition of by-products of the principal process technology in a multistage process, the by-products being selected from the group consisting of o,p isomers of bisphenol A, Dianin compound, trisphenols, polyphenols and colored substances, wherein unit (1) of the reaction system is the unit where the following reactions are conducted simultaneously: reaction of phenol with acetone, reaction of phenol with recycled p-isopropenylphenol, and reactions of isomerizational rearrangement of bisphenol A isomers, at a temperature of about 60°-95° C. in the presence of a micro- and macroporous catalyst mixture, whereas the post-reaction mixture is cooled together with acetone and water to obtain a bisphenol-A/phenol slurry adduct in a phenolic solution in unit (2) and the bisphenol-A/phenol slurry adduct in a phenolic solution obtained in unit (2) is separated in unit (3) to obtain crystalline bisphenol-A/phenol adduct and phenol liquor I, whereafter the crystalline adduct is washed with phenolic solution and the crystalline bisphenol-A/phenol adduct obtained in unit (3) is dissolved in at least one of a portion of the phenol liquor I and a phenol liquor II in unit (4) and the mixture is cooled to obtain bisphenol-A/phenol adduct slurry in a phenolic solution, whereafter the slurry obtained in unit (4) is separated in unit (5) into crystalline bisphenol-A/phenol adduct and the phenol liquor II to be sent back to unit (3) while washing the crystalline bisphenol-A/phenol adduct with phenol solution, whereas the high-purity bisphenol A is separated in unit (6) by removing phenol from bisphenol-A/phenol adduct obtained in unit (5), phenol liquor I obtained in unit (3) is distilled in unit (7) by removing water and acetone and part of phenol therefrom, whereas dewartered phenol liquor is sent back to unit (1), whereafter part of the phenol liquor obtained in at least one of unit (3) and unit (7) is decomposed by thermal catalytic decomposition in unit (8) to obtain phenol-containing distillate, p-isopropenylphenol and the process by-products, while reactive components of the distillate obtained in unit (8) are rearranged catalytically in unit (9) leaving the p-isopropenylphenol contained therein substantially intact, and the rearranged distillate is sent back to unit (1) of the process of the invention.

2. A process for preparing bisphenol A, comprising the steps of:
(a) simultaneously (1) reacting phenol with acetone, (2) reacting p-isopropenylphenol with phenol, and (3) subjecting isomers of bisphenol A to isomerization in a single reactant mixture containing a strong acid cation-exchange resin catalyst at a temperature of about 60°–95° C. to form a post-reaction mixture containing bisphenol A and phenol, the bisphenol A being produced in each of reactions (1)–(3),
(b) cooling the post-reaction mixture to form a first slurry containing a first bisphenol A-phenol adduct,
(c) subjecting the first slurry to solid-liquid separation to obtain a first crystalline bisphenol A-phenol adduct and a first phenolic solution,
(d) removing water and phenol from at least a portion of the first phenolic solution to form a dewatered first phenolic solution, and recycling a portion of the dewatered first phenolic solution into the reactant mixture of step (a),
(e) washing the first crystalline bisphenol A-phenol adduct with a portion of a second phenolic solution,
(f) dissolving the washed first crystalline bisphenol A-phenol adduct in at least one of a portion of the dewatered first phenolic solution and a portion of the second phenolic solution,
(g) cooling the dissolved mixture from step (f) to form a second slurry containing a second bisphenol A-phenol adduct,
(h) subjecting the second slurry to solid-liquid separation to obtain the second phenolic solution, at least a portion of which is recycled to step (e), and a second crystalline bisphenol A-phenol adduct,
(i) washing the second crystalline bisphenol A-phenol adduct with a third phenolic solution,
(j) removing phenol from the washed second crystalline bisphenol A-phenol adduct to obtain bisphenol A, and
(k) treating the non-watered portion of the first phenolic solution and any remaining portion of the dewatered first phenolic solution to obtain a distillate comprising phenol, p-isopropenylphenol and isomers of bisphenol A, and recycling the distillate to step (a).

3. A process according to claim 2, wherein only non-dewatered phenolic solution is treated in step (k).

4. A process according to claim 2, wherein step (k) comprises subjecting the non-dewatered portion of the first phenolic solution and any remaining portion of the dewatered first phenolic solution to thermal catalytic decomposition.

5. A process as claimed in claim 4, wherein step (k) further comprises the step of subsequently catalytically rearranging the distillate, leaving the p-isopropenylphenol substantially intact.

6. A process as claimed in claim 2, wherein the reactant mixture of step (a) contains about 10–30 wt % by-products comprising at least one member of the group consisting of isomers of bisphenol A, Dianin compound, trisphenols, polyphenols, and colored substances.

7. A process according to claim 2, wherein the post-reaction mixture contains about 15–35 wt % bisphenol A.

8. A process according to claim 2, wherein the post-reaction mixture contains about 20–30 wt % bisphenol A.

9. A process according to claim 2, wherein the first slurry of step (b) contains about 2–6 wt % acetone and about 1–4 wt % water.

10. A process according to claim 2, wherein the first crystalline bisphenol A-phenol adduct is washed in step (e) with the second phenolic solution in a amount of about 0.2–2.0 parts by weight of second phenolic solution per 1 part by weight of adduct.

11. A process according to claim 2, wherein the third phenolic solution used in step (i) comprises about 1–3 parts by weight fresh phenol per 1 part by weight phenol which is removed in step (j).

12. A process according to claim 2, wherein phenol is removed from the washed second crystalline bisphenol A-phenol adduct by vacuum distillation and steam stripping.

13. A process according to claim 2, wherein step (d) comprises a distillation process in which phenol is removed from the first phenolic solution in an amount of about 0.1–0.3 parts by weight of phenol per part by weight of first phenolic solution.

14. A process according to claim 4, wherein the non-dewatered portion of the first phenolic solution is about 0.05–0.2 parts by weight of the first phenolic solution obtained in step (c).

15. A process according to claim 4, wherein the thermal catalytic decomposition is conducted at a temperature of about 200°–300° C. in the presence of a catalyst comprising at least one member selected from the group consisting of $Na_2HPO_2$, $NaHCO_3$, $Na_2CO_3$ and NaOH.

16. A process according to claim 5, wherein catalytic rearrangement is effected in the presence of 0.05–0.5% by weight of oxalic acid.

17. A process according to claim 4, wherein the third phenolic solution of step (i) comprises fresh phenol.

18. A process according to claim 4, wherein the third phenolic solution of step (i) consists essentially of fresh phenol and removed phenol from step (j) in a ratio of 1–3 parts by weight fresh phenol per 1 part by weight removed phenol from step (j).

19. A process according to claim 2, wherein the reactant mixture of step (a) contains about 10–30 wt % by-products comprising at least 1 member of the group consisting of isomers of bisphenol A, Dianin compound, trisphenols, polyphenols and colored substances, the post-reaction mixture contains about 15–35 wt % bisphenol A, the first slurry of step (b) contains about 2–6 wt % acetone and about 1–4 wt % water, step (d) comprises a distillation process in which phenol is removed from the first phenolic solution in an amount of about 0.1–0.3 parts by weight of phenol per part by weight of first phenolic solution, the first crystalline bisphenol A-phenol adduct is washed in step (e) with the second phenolic solution in an amount of about 0.2-2.0 parts by weight of second phenolic solution per 1 part by weight of adduct, and the third phenolic solution of step (i) consists essentially of fresh phenol and removed phenol from step (j) in a ratio of 1-3 parts by weight fresh phenol per 1 part by weight removed phenol from step (j).

20. A process according to claim 5, wherein the non-dewatered portion of the first phenolic solution is about 0.05-0.2 parts by weight of the first phenolic solution obtained in step (c), and the thermal catalytic decomposition is conducted at a temperature of about 200°-300° C. in the presence of a catalyst comprising at least one member selected from the group consisting of $Na_2HPO_2$, $NaHCO_3$, $Na_2CO_3$ and $NaOH$.

* * * * *